US00PP27120P2

(12) United States Plant Patent
Davey et al.

(10) Patent No.: US PP27,120 P2
(45) Date of Patent: Aug. 30, 2016

(54) ***HELLEBORUS* PLANT NAMED 'RD06'**

(50) Latin Name: *Helleborus×hybridus*
Varietal Denomination: RD06

(71) Applicants: Rodney Davey, Axminster (GB); Lynda Windsor, Axminster (GB)

(72) Inventors: Rodney Davey, Axminster (GB); Lynda Windsor, Axminster (GB)

( * ) Notice: Subject to any disclaimer, the term of this patent is extended or adjusted under 35 U.S.C. 154(b) by 96 days.

(21) Appl. No.: 14/121,964

(22) Filed: Nov. 7, 2014

(51) Int. Cl.
*A01H 5/02* (2006.01)

(52) U.S. Cl.
USPC ..... Plt./439

(58) Field of Classification Search
USPC ..... Plt./439
See application file for complete search history.

*Primary Examiner* — Susan McCormick Ewoldt
(74) *Attorney, Agent, or Firm* — C. A. Whealy

(57) ABSTRACT

A new and distinct cultivar of *Helleborus* plant named 'RD06', characterized by its upright and mounding plant habit; variegated developing leaves; uniform, continuous and freely flowering habit; green and purple-colored flowers held above the foliar plane on relatively long peduncles; and good garden performance.

1 Drawing Sheet

Botanical designation: *Helleborus×hybridus.*
Cultivar denomination: 'RD06'.

BACKGROUND OF THE INVENTION

The present invention relates to a new and distinct cultivar of *Helleborus* plant, botanically known as *Helleborus×hybridus* and hereinafter referred to by the name 'RD06'.

The new *Helleborus* plant is a product of a planned breeding program conducted by the Inventors in Devon, United Kingdom. The objective of the breeding program was to create new freely-flowering *Helleborus* plants with strong peduncles that hold attractive flowers above the foliar plane.

The new *Helleborus* plant originated from a cross-pollination conducted by the Inventors in Devon, United Kingdom in January, 2009 of a proprietary seedling selection of *Helleborus×hybridus* identified as code designation EXC14069, as the female, or seed, parent, not patented, with a proprietary seedling selection of *Helleborus×hybridus* identified as code designation OR3863, as the male, or pollen, parent, not patented. The new *Helleborus* plant was discovered and selected by the Inventors as a single flowering plant from within the progeny of the stated cross-pollination grown in a controlled greenhouse environment in Devon, United Kingdom in February, 2011.

Asexual reproduction of the new *Helleborus* plant by tissue culture in a controlled greenhouse environments in Roelofarendsveen, The Netherlands since March, 2011, has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype of the new *Helleborus* plant may vary somewhat with variations in environmental conditions such as temperature and light intensity without, however, any variance in genotype of the new *Helleborus* plant.

The following traits have been repeatedly observed and are determined to be the unique characteristics of 'RD06'. These characteristics in combination distinguish 'RD06' as a new and distinct *Helleborus* plant:

1. Upright and mounding plant habit.
2. Variegated developing leaves.
3. Uniform, continuous and freely flowering habit.
4. Green and purple-colored flowers held above the foliar plane on relatively long peduncles.
5. Good garden performance.

Plants of the new *Helleborus* differ from plants of the female parent selection in the following characteristics:

1. Plants of the new *Helleborus* are taller than plants of the female parent selection.
2. Plants of the new *Helleborus* and the female parent selection differ in flower color as plants of the female parent selection have whitish green-colored flowers.

Plants of the new *Helleborus* differ from plants of the male parent selection in the following characteristics:

1. Plants of the new *Helleborus* are shorter than plants of the male parent selection.
2. Plants of the new *Helleborus* and the male parent selection differ in flower color as plants of the male parent selection have red-colored flowers.

Plants of the new *Helleborus* can be compared to plants of *Helleborus×hybridus* 'ABCRD01', disclosed in U.S. Plant Pat. No. 24,149. In side-by-side comparisons conducted in Devon, United Kingdom, plants of the new *Helleborus* differed from plants of 'ABCRD01' in the following characteristics:

1. Plants of the new *Helleborus* were taller than plants of 'ABCRD01'.
2. Plants of the new *Helleborus* had larger leaves than plants of 'ABCRD01'.
3. Plants of the new *Helleborus* had variegated developing leaves whereas plants of 'ABCRD01' had solid green-colored developing leaves.
4. Plants of the new *Helleborus* had larger flowers and larger inflorescences than plants of 'ABCRD01'.

5. Plants of the new *Helleborus* and 'ABCRD01' differed in flower color as plants of 'ABCRD01' had red purple-colored flowers.
6. Plants of the new *Helleborus* had longer peduncles and pedicels than plants of 'ABCRD01'.

BRIEF DESCRIPTION OF THE PHOTOGRAPH

The accompanying colored photograph illustrates the overall appearance of the new *Helleborus* plant showing the colors as true as it is reasonably possible to obtain in colored reproductions of this type, Colors in the photograph may differ slightly from the color values cited in the detailed botanical description which accurately describe the colors of the new *Helleborus* plant. The photograph comprises a close-up view of a typical flowering plant of 'RD06'.

DETAILED BOTANICAL DESCRIPTION

The aforementioned photograph and following observations, measurements and values describe plants grown during the winter in three-liter containers in an outdoor nursery in Boijl, The Netherlands and under cultural practices typical of commercial *Helleborus* production. During the production of the plants, day temperatures ranged from 0° C. to 10° C. and night temperatures ranged from −15° C. to 0° C. Plants were one year old when the photograph and the description were taken. In the following description, color references are made to The Royal Horticultural Society Colour Chart, 2001 Edition, except where general terms of ordinary dictionary significance are used.

Botanical classification: *Helleborus hybridus* 'RD06'.

Parentage:

*Female, or seed, parent*.—Proprietary seedling selection of *Helleborus×hybridus* identified as code designation EXC14069, not patented.

*Male, or pollen, parent*.—Proprietary seedling selection of *Helleborus×hybridus* identified as code designation OR3863, not patented.

Propagation:

*Type*.—By tissue culture.

*Time to initiate roots, summer*.—About 15 days at temperatures about 22° C. to 25° C.

*Time to produce a rooted young plant, summer*.—About two months at temperatures about 20° C.

*Root description*.—Fleshy, vigorous; white to brown in color.

Plant description:

*Plant and growth habit*.—Herbaceous perennial; upright and mounding plant habit with flowers held above the foliar plane; moderately vigorous to vigorous growth habit.

*Plant height*.—About 35 cm to 45 cm.

*Plant diameter* (*area of spread*).—About 20 cm to 30 cm.

Leaf description:

*Arrangement*.—Leaves arranged alternately in a basal rosette; leaves palmately compound with three to five leaflets per leaf.

*Leaflet length*.—About 10 cm to 15 cm.

*Leaflet width*.—About 6 cm to 8 cm.

*Leaflet shape*.—Palmate; elliptic to ovate.

*Leaflet apex*.—Acute.

*Leaflet base*.—Cordate to acute.

*Leaflet margin*.—Dentate to serrate.

*Leaflet texture, upper and lower surfaces*.—Smooth, glabrous; leathery.

*Leaflet venation pattern*.—Pinnate.

*Leaflet color*.—Developing leaves, upper surface: Close to 139A; central spots, close to 191B; center becoming closer to N187C with development. Developing leaves, lower surface: Close to 138A slightly overlain with close to N187A. Fully expanded leaves, upper surface: Close to 139A; venation, close to 139C, distally, close to 187A. Fully expanded leaves, lower surface: Close to 138A; venation, close to 139B, distally, close to N199A.

*Petioles*.—Length: About 15 cm to 25 cm. Diameter: About 4 mm to 8 mm. Texture, upper and lower surfaces: Smooth, glabrous. Color, developing leaves, upper and lower surfaces: Close to 138A; spots, close to 187A. Color, fully expanded leaves, upper and lower surfaces: Close to 138A; spots, close to N199A.

Flower description:

*Flower shape and habit*.—Single-type rotate flowers arranged in loosely branched cymes; freely flowering habit with typically about 10 to 15 flowers developing per cyme and up to 40 flowers developing per cyme in the second year of growth; flowers facing outwardly.

*Fragrance*.—None detected.

*Natural flowering season*.—Plants begin flowering about two months after planting; plants flower from January until March in the United Kingdom.

*Flower longevity on the plant*.—About two months; flowers persistent.

*Inflorescence height*.—About 40 cm to 60 cm.

*Inflorescence diameter*.—About 30 cm to 40 cm.

*Flower buds*.—Length: About 2 cm to 3 cm. Diameter: About 1 cm to 2 cm. Shape: Elliptic to ovate. Color: Close to N77D.

*Flower diameter*.—About 8 cm.

*Flower depth* (*height*).—About 2 cm to 4 cm.

*Petals*.—None observed; transformed into nectaries.

*Sepals*.—Quantity and arrangement: Five arranged in a single whorl. Length: About 5 cm. Width: About 3 cm to 4.5 cm. Shape: Elliptic to obovate. Apex: Rounded to obtuse. Base: Rounded to obtuse Margin: Entire. Texture, upper and lower surfaces: Smooth, glabrous. Color: When opening, upper surface: Close to N77D; center, close to 138B. When opening, lower surface: Close to 146C. Fully opened, upper surface: Close to 138B; towards the margins, slightly tinged with close to N77D. Fully opened, lower surface: Close to 146C.

*Peduncles*.—Length: About 20 cm to 30 cm. Diameter: About 5 mm to 10 mm. Strength: Strong. Aspect: Mostly upright. Texture: Smooth, glabrous. Color: Close to 138A; spots, close to 187A.

*Pedicels*.—Length: About 5 cm to 10 cm. Diameter: About 3 mm to 4 mm. Aspect: About 10° from peduncle axis. Strength: Strong. Texture: Smooth, glabrous. Color: Close to 138A; spots, close to 187A.

*Reproductive organs*.—Stamens: Quantity per flower: About 40 to 60. Filament length: About 1.5 cm to 1.8 cm. Filament color: Close to 4D. Anther shape: Elliptic to ovate. Anther length: About 2 mm. Anther color: Close to 4A. Pollen amount: Scarce. Pollen color: Close to 4A. Pistils: Quantity per flower: About five. Pistil length: About 2.5 cm. Stigma shape: Clubshaped. Stigma color: Close to 4B. Style length: About 1.5 cm. Style color: Close to 183A. Ovary color: Close to 183A.

*Nectaries*.—Quantity per flower: About 10 to 14. Length: About 5 mm to 7 mm. Width: About 2 mm to 5 mm. Shape: Funnelform. Color: Close to N144C; towards the apex, close to 149B.

*Seeds and fruits*.—Seed and fruit development have not been observed on plants of the new *Helleborus*.

Garden performance: Plants of the new *Helleborus* have been observed to have good garden performance and to tolerate rain, wind and temperatures ranging from about −10° C. to about 35° C.

Pathogen & pest resistance: Plants of the new *Helleborus* have not been observed to be resistant to pathogens and pests common to *Helleborus* plants.

It is claimed:

1. A new and distinct *Helleborus* plant named 'RD06' as illustrated and described.

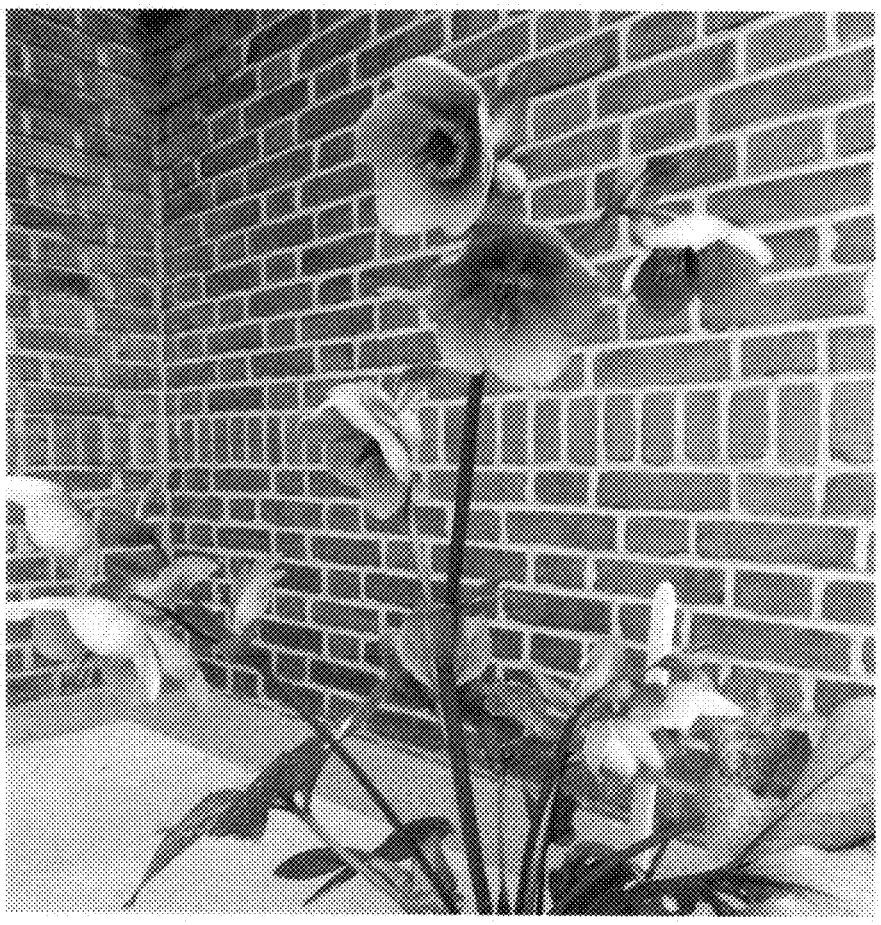

* * * * *